US008428690B2

(12) United States Patent
Li et al.

(10) Patent No.: US 8,428,690 B2
(45) Date of Patent: Apr. 23, 2013

(54) INTRACARDIAC ECHOCARDIOGRAPHY IMAGE RECONSTRUCTION IN COMBINATION WITH POSITION TRACKING SYSTEM

(75) Inventors: Dun Alex Li, Salem, NH (US); Christopher A. Nafis, Rexford, NY (US); Douglas G. Wildes, Ballston Lake, NY (US); Vernon T. Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 798 days.

(21) Appl. No.: 12/060,714

(22) Filed: Apr. 1, 2008

(65) Prior Publication Data

US 2008/0287803 A1    Nov. 20, 2008

Related U.S. Application Data

(60) Provisional application No. 60/938,442, filed on May 16, 2007.

(51) Int. Cl.
*A61B 5/05* (2006.01)

(52) U.S. Cl.
USPC ........... 600/424; 600/407; 600/426; 600/415; 600/428; 600/437; 600/443; 600/463; 382/128

(58) Field of Classification Search .................. 600/407, 600/424, 428, 437
See application file for complete search history.

(56) References Cited

U.S. PATENT DOCUMENTS

| RE30,397 E | 9/1980 | King |
| 4,672,963 A | 6/1987 | Barken |
| 4,706,681 A | 11/1987 | Breyer et al. |
| 4,722,056 A | 1/1988 | Roberts et al. |

(Continued)

FOREIGN PATENT DOCUMENTS

| DE | 103 40 546 A1 | 3/2005 |
| EP | 0602730 | 6/1994 |

(Continued)

OTHER PUBLICATIONS

Kanckstedt, C. et al, "Semi-Automated 3-Dimensional Intracardiac Echocardiography: Development and Initial Clinical Experience of a New System to Guide Ablation Procedures", Heart Rhythm, 3 (12), pp. 1453-1459, 2006.

(Continued)

*Primary Examiner* — Tse Chen
*Assistant Examiner* — Baisakhi Roy
(74) *Attorney, Agent, or Firm* — The Small Patent Law Group; Dean D. Small

(57) ABSTRACT

A system and method to display a four-dimensional (4D) model of an imaged anatomy is provided. The system comprises a controller, and an imaging system including an imaging probe in communication with the controller. The imaging probe can acquire generally real-time, 3D image data relative to a direction of image acquisition along an imaging plane. The system also includes a tracking system in communication with the controller. The tracking system includes at least one tracking element integrated with the imaging probe. The system is operable to process the generally real-time, 3D image data acquired by the imaging probe relative to generally real-time tracking information acquired by the tracking system so as to display the 4D model of the imaged anatomy.

29 Claims, 5 Drawing Sheets

U.S. PATENT DOCUMENTS

| | | | |
|---|---|---|---|
| 4,750,367 A | 6/1988 | Bernatets | |
| 4,821,731 A | 4/1989 | Martinelli et al. | |
| 4,834,089 A | 5/1989 | Koivukangas et al. | |
| 4,869,256 A | 9/1989 | Kanno et al. | |
| 4,896,673 A | 1/1990 | Rose et al. | |
| 5,099,846 A | 3/1992 | Hardy | |
| 5,135,001 A | 8/1992 | Sinofsky et al. | |
| 5,203,337 A | 4/1993 | Feldman | |
| 5,241,473 A | 8/1993 | Ishihara et al. | |
| 5,353,354 A | 10/1994 | Keller et al. | |
| 5,370,120 A | 12/1994 | Oppelt et al. | |
| 5,383,454 A | 1/1995 | Bucholz | |
| 5,391,139 A | 2/1995 | Edmundson | |
| 5,391,199 A | 2/1995 | Ben-Haim | |
| 5,409,000 A | 4/1995 | Imran | |
| 5,409,007 A | 4/1995 | Saunders et al. | |
| 5,432,544 A | 7/1995 | Ziarati | |
| 5,438,997 A | 8/1995 | Sieben et al. | |
| 5,447,154 A | 9/1995 | Cinquin et al. | |
| 5,517,990 A | 5/1996 | Kalfas et al. | |
| 5,531,520 A | 7/1996 | Grimson et al. | |
| 5,558,091 A | 9/1996 | Acker et al. | |
| 5,568,384 A | 10/1996 | Robb et al. | |
| 5,568,809 A | 10/1996 | Ben-Haim | |
| 5,579,764 A | 12/1996 | Goldreyer | |
| 5,588,432 A | 12/1996 | Crowley | |
| 5,608,849 A | 3/1997 | King | |
| 5,633,951 A | 5/1997 | Moshfeghi | |
| 5,662,108 A | 9/1997 | Budd et al. | |
| 5,682,890 A | 11/1997 | Kormos | |
| 5,687,737 A | 11/1997 | Branham et al. | |
| 5,713,946 A | 2/1998 | Ben-Haim | |
| 5,740,802 A | 4/1998 | Nafis et al. | |
| 5,765,561 A | 6/1998 | Chen et al. | |
| 5,771,895 A | 6/1998 | Slager | |
| 5,787,886 A | 8/1998 | Kelly | |
| 5,800,352 A | 9/1998 | Ferre et al. | |
| 5,810,008 A | 9/1998 | Dekel et al. | |
| 5,823,958 A | 10/1998 | Truppe | |
| 5,840,031 A | 11/1998 | Crowley | |
| 5,891,034 A | 4/1999 | Bucholz | |
| 5,924,989 A | 7/1999 | Polz | |
| 5,938,602 A | 8/1999 | Lloyd | |
| 5,957,941 A | 9/1999 | Ream | |
| 5,961,454 A | 10/1999 | Kooy et al. | |
| 5,967,980 A | 10/1999 | Ferre et al. | |
| 5,978,696 A | 11/1999 | VomLehn et al. | |
| 5,999,840 A | 12/1999 | Grimson et al. | |
| 6,006,126 A | 12/1999 | Cosman | |
| 6,016,439 A | 1/2000 | Acker | |
| 6,019,725 A | 2/2000 | Vesely et al. | |
| 6,073,043 A | 6/2000 | Schneider | |
| 6,086,532 A | 7/2000 | Panescu et al. | |
| 6,102,863 A | 8/2000 | Pflugrath et al. | |
| 6,120,453 A * | 9/2000 | Sharp | 600/463 |
| 6,149,592 A | 11/2000 | Yanof et al. | |
| 6,168,565 B1 | 1/2001 | Napolitano | |
| 6,200,269 B1 | 3/2001 | Lin et al. | |
| 6,203,497 B1 | 3/2001 | Dekel et al. | |
| 6,216,027 B1 | 4/2001 | Willis et al. | |
| 6,226,543 B1 | 5/2001 | Gilboa et al. | |
| 6,235,038 B1 | 5/2001 | Hunter et al. | |
| 6,246,898 B1 | 6/2001 | Vesely et al. | |
| 6,259,942 B1 | 7/2001 | Westermann et al. | |
| 6,259,943 B1 | 7/2001 | Cosman et al. | |
| 6,325,759 B1 | 12/2001 | Pelissier | |
| 6,351,573 B1 | 2/2002 | Schneider et al. | |
| 6,379,302 B1 | 4/2002 | Kessman et al. | |
| 6,389,311 B1 | 5/2002 | Whayne et al. | |
| 6,413,219 B1 | 7/2002 | Avila et al. | |
| 6,447,450 B1 | 9/2002 | Olstad | |
| 6,490,474 B1 | 12/2002 | Willis et al. | |
| 6,505,063 B2 | 1/2003 | Van Den Brink et al. | |
| 6,514,249 B1 | 2/2003 | Maguire et al. | |
| 6,537,217 B1 | 3/2003 | Bjaerum et al. | |
| 6,575,901 B2 | 6/2003 | Stoycos et al. | |
| 6,650,927 B1 | 11/2003 | Keidar | |
| 6,669,635 B2 | 12/2003 | Kessman et al. | |
| 6,679,847 B1 | 1/2004 | Robinson et al. | |
| 6,705,992 B2 | 3/2004 | Gatzke | |
| 6,716,166 B2 | 4/2004 | Govari | |
| 6,728,562 B1 | 4/2004 | Budd et al. | |
| 6,773,408 B1 | 8/2004 | Acker et al. | |
| 6,775,404 B1 | 8/2004 | Pagoulatos et al. | |
| 6,776,402 B2 | 8/2004 | Miyamoto et al. | |
| 6,902,528 B1 | 6/2005 | Garibaldi et al. | |
| 6,950,689 B1 | 9/2005 | Willis et al. | |
| 7,090,639 B2 | 8/2006 | Govari | |
| 7,156,816 B2 | 1/2007 | Schwartz et al. | |
| 7,263,397 B2 | 8/2007 | Hauck et al. | |
| 7,270,634 B2 | 9/2007 | Scampini et al. | |
| 7,285,117 B2 | 10/2007 | Krueger et al. | |
| 7,314,446 B2 | 1/2008 | Byrd et al. | |
| 7,379,769 B2 * | 5/2008 | Piron et al. | 600/415 |
| 7,485,115 B2 | 2/2009 | Nakamura | |
| 7,599,730 B2 * | 10/2009 | Hunter et al. | 600/424 |
| RE41,066 E | 12/2009 | Martinelli et al. | |
| 7,657,300 B2 | 2/2010 | Hunter et al. | |
| 7,697,972 B2 * | 4/2010 | Verard et al. | 600/424 |
| 7,844,320 B2 | 11/2010 | Shahidi | |
| 7,871,406 B2 * | 1/2011 | Nields et al. | 606/27 |
| 7,940,972 B2 * | 5/2011 | Wildes et al. | 382/128 |
| 2001/0029334 A1 | 10/2001 | Graumann et al. | |
| 2002/0005719 A1 | 1/2002 | Gilboa et al. | |
| 2002/0026118 A1 | 2/2002 | Govari | |
| 2002/0042571 A1 | 4/2002 | Gilboa et al. | |
| 2003/0013958 A1 | 1/2003 | Govari et al. | |
| 2003/0045795 A1 | 3/2003 | Bjaerum et al. | |
| 2003/0074011 A1 | 4/2003 | Gilboa et al. | |
| 2003/0120318 A1 | 6/2003 | Hauck | |
| 2003/0163045 A1 | 8/2003 | Gatzke | |
| 2003/0176778 A1 | 9/2003 | Messing et al. | |
| 2003/0208102 A1 | 11/2003 | Gilboa | |
| 2004/0097806 A1 | 5/2004 | Hunter et al. | |
| 2004/0102769 A1 | 5/2004 | Schwartz et al. | |
| 2004/0127798 A1 | 7/2004 | Dala-Krishna et al. | |
| 2004/0138548 A1 | 7/2004 | Strommer et al. | |
| 2004/0147842 A1 | 7/2004 | Desmarais | |
| 2004/0152974 A1 | 8/2004 | Solomon | |
| 2004/0162507 A1 | 8/2004 | Govari | |
| 2004/0162550 A1 | 8/2004 | Govari et al. | |
| 2004/0249259 A1 | 12/2004 | Heimdal et al. | |
| 2004/0254458 A1 | 12/2004 | Govari | |
| 2005/0080333 A1 * | 4/2005 | Piron et al. | 600/417 |
| 2005/0080336 A1 | 4/2005 | Byrd et al. | |
| 2005/0090745 A1 | 4/2005 | Steen | |
| 2005/0096543 A1 | 5/2005 | Jackson et al. | |
| 2005/0131474 A1 | 6/2005 | Byrd et al. | |
| 2005/0165279 A1 | 7/2005 | Adler et al. | |
| 2005/0171428 A1 | 8/2005 | Fichtinger et al. | |
| 2005/0197557 A1 | 9/2005 | Strommer et al. | |
| 2005/0203375 A1 | 9/2005 | Willis et al. | |
| 2006/0041180 A1 | 2/2006 | Viswanathan et al. | |
| 2006/0182320 A1 | 8/2006 | Peszynski et al. | |
| 2006/0184016 A1 | 8/2006 | Glossop | |
| 2006/0229594 A1 | 10/2006 | Francischelli et al. | |
| 2006/0239540 A1 * | 10/2006 | Serra et al. | 382/154 |
| 2006/0241432 A1 * | 10/2006 | Herline et al. | 600/437 |
| 2006/0241445 A1 | 10/2006 | Altmann et al. | |
| 2006/0253024 A1 | 11/2006 | Altmann et al. | |
| 2006/0253029 A1 | 11/2006 | Altmann et al. | |
| 2006/0253030 A1 | 11/2006 | Altmann et al. | |
| 2006/0253031 A1 | 11/2006 | Altmann et al. | |
| 2006/0253032 A1 | 11/2006 | Altmann et al. | |
| 2006/0287890 A1 | 12/2006 | Stead et al. | |
| 2007/0130287 A1 | 6/2007 | Kumar et al. | |
| 2007/0287902 A1 | 12/2007 | Fuimaono et al. | |
| 2008/0123923 A1 * | 5/2008 | Gielen et al. | 382/131 |
| 2008/0177994 A1 | 7/2008 | Mayer | |
| 2008/0242978 A1 * | 10/2008 | Simon et al. | 600/426 |
| 2008/0269588 A1 * | 10/2008 | Csavoy et al. | 600/407 |
| 2009/0163810 A1 * | 6/2009 | Kanade et al. | 600/443 |

FOREIGN PATENT DOCUMENTS

| | | |
|---|---|---|
| EP | 1 637 070 A | 3/2005 |
| WO | 9107726 | 5/1991 |
| WO | WO 92/19157 | 11/1992 |

| | | |
|---|---|---|
| WO | 9625881 | 8/1996 |
| WO | 9729682 | 8/1997 |
| WO | 9824065 | 6/1998 |
| WO | 9835720 | 8/1998 |
| WO | 9900052 | 1/1999 |
| WO | 9958055 | 11/1999 |
| WO | 0023000 | 4/2000 |
| WO | 0056215 | 9/2000 |
| WO | WO 01/20552 A1 | 3/2001 |
| WO | 0134050 | 5/2001 |

OTHER PUBLICATIONS

Proulx, T.L. et al, "Advances in Catheter-Based Ultrasound Imaging", IEEE International Ultrasonics Symposium Proceedings, 2005.

Rotger, D. et al, "Multimodal Registration of Intravascular Ultrasound Images and Angiography", Computer Vision Center Universitat Autonoma de Barcelona Bellaerra, Spain, www.cvc.uab.es/~petia/caseib2002.pdf.

Huang, X. et al, "Dynamic 3D Ultrasound and MR Image Registration of the Beating Heart", MICAI, LNCS 3750, pp. 171-178, 2005.

Martin, R. et al, "A Miniature Position and Orientation Locator for Three Dimensional Echocardiography", IEEE Proceedings on Computer in Cardiology, pp. 25-28, 1993.

Beaseley, R.A. et al, "Registration of ultrasound images", www.tgt.vanderbilt.edu/archive/registration of ultrasound images.pdf.

Leotta, D.F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Ineractive 3-D Registration of Ultrasound and Magnetic Resonance Images Based on a Magnetic Position Sensor", IEEE on Info. Tech. In Biomedicine, vol. 3, No. 4, 1999.

"Catheter Ablation", Cleveland Clinic—Heart & Vascular Institute, http://www.clevelandclinic.org/heartcenter/pub/guide/tests/procedures/ablation.htm, Apr. 2005.

Stoll, J et al, "Passive Markers for Ultrasound Tracking of Surgical Instruments", MICCAI, LNCS 3750, pp. 41-48, 2005.

Beasley R. A. et al; "Registration of ultrasound images"; 8 pgs.

Bricault Ivan et al; "Registration of Real and CT-Derived Virtual Bronchoscopic Images to Assist Transbronchial Biopsy"; IEEE Transactions on Medical Imaging, Vol. 17, No. 5, Oct. 1998; 12 pgs.

"Catheter Ablation"; Heart and Vascular Institute; www.clevelandclinic.org/heartcenter; 5 pgs.

Grimson W.E.L. et al; "An Automatic Registration Method for Frameless Stereotaxy, Image Guided Surgery, and Enhanced Reality Visualization": IEEE Transactions on Medical Imaging, vol. 15, No. 2, Apr. 1996; 12 pgs.

Reinhardt, H. et al; "Computer aided surgery with special focus on neuronavigation" Computerized Medical Imaging and Graphics 23(1999) 237-244; www.elsevier.com; 8 pgs.

Huang, Xishi et al; "Dynamic 3D Ultrasound and MR Image Registration of the Beating Heart"; 8 pgs.

Yamashita Juli et al; "Real-Time 3-D Model-Based Navigation System for Endoscopic Paranasal Sinus Surgery"; IEEE Transactions on Biomedical Engineering vol. 46, No. 1, Jan. 1999; 11 pgs.

Knackstedt, Christian MD et al; "Semi-automated 3-dimensional intracardiac echocardiography: Development and initial clinical experience of a new system to guide ablation procedures" 1547-5271/$—see front matter © 2006 Heart Rhythm Society; 7 pgs.

Leotta, Daniel F. et al; "Three-Dimensional Ultrasound Imaging Using Multiple Magnetic Tracking Systems and Miniature Magnetic Sensors"; IEEE Ultrasonics Symposium 1995; 4 pgs.

Lewis, Judith Thomas et al; "An Ultrasonic Approach to Localization of Fiducial Markers for Interactive, Image-Guided Neurosurgery—Part I: Principles" IEEE Transactions on Biomedical Engineering, vol. 45, No. 5, May 1998; 11 pgs.

Pagoulatos, Niko et al; "Interactive 3-D Registration of Ultrasound and Magnetic Resonance Images Based on a Magnetic Position Sensor"; IEEE Transactions on Technology in Biomedicine, vol. 3, No. 4, Dec. 1999; 11 pgs.

Roberts, David W.; "The Future of Frameless Stereotaxy"; Chapter 214, Textbook of Steriotactic and Functional Neurosurgery; McGraw-Hill 1998; 11 pgs.

St-Jean, Philippe et al; "Automated Atlas Integration and Interactive Three-Dimenstional Visualization Tools for Planning and Guidance in Functional Neurosurgery"; IEEE Transactions on Medical Imaging, vol. 17, No. 5, Oct. 1998; 9 pgs.

Proulx, T. L. et al; "Advances in Catheter-Based Ultrasound Imaging Intracardiac Echocardiography and the ACUSON AcuNav(TM) Ultrasound Catheter"; IEEE International Ultrasonics Symposium 1995; 10 pgs.

Sato, Yoshinobu Sato et al; "Image Guidance of Breast Cancer Surgery Using 3-D Ultrasound Images and Augmented Reality Visualization"; IEEE Transactions on Medical Imaging, vol. 17, No. 5, Oct. 1998, 13 pgs.

Schreiner, Steven et al; "An Ultrasonic Approach to Localization of Fiducial Markers for Interactive, Image-Guided Neurosurgery—Part II: Implementation and Automation"; IEEE Transactions on Biomedical Engineering, vol. 45, No. 5, May 1998; 11 pgs.

Stoll, Jeffrey et al; "Passive Markers for Ultrasound Tracking of Surgical Instruments"; J. Duncan and G. Gerig (Eds.): MICCAI 2005, LNCS 3750, pp. 41-48, 2005. © Springer-Verlag Berlin Heidelberg 2005; 8 pgs.

Birkfellner, Wolfgang et al; "Calibration of Tracking Systems in a Surgical Environment"; IEEE Transactions on Medical Imaging, vol. 17, No. 5, Oct. 1998; 6 pgs.

Yamashita Juli et al; "A 3-D Navigation System for Endoscopic Sinus Surgery"; 8 pgs.

Office Action dated Feb. 5, 2008; U.S. Appl. No. 11/182,910, filed Jul. 15, 2008; Applicant: Donaldson et al.; 10 pages.

Office Action dated Feb. 28, 2008; U.S. Appl. No. 11/433,951, filed May 15, 2006; Applicant: Donaldson; 11 pages.

Office Action dated Jan. 16, 2008; U.S. Appl. No. 11/182,473, filed Jul. 15, 2008; Applicant: Donaldson; 11 pages.

A. Milkowski et al. "Speckle Reduction Imaging"; Technical White Paper—General Electric Health Care (Ultrasound). Last accessed on Jul. 9, 2009. Available at http:www.gehealthcare.com/usen/ultrasound/education/docs/whitepaper_SRI.pdf.

http://medical.merrian-webster.com/medical/m-mode.

Radiology, vol. 121, 157-162, Copyright © 1976 by Radiological Society of North America.

* cited by examiner

INTRACARDIAC ECHOCARDIOGRAPHY IMAGE RECONSTRUCTION IN COMBINATION WITH POSITION TRACKING SYSTEM

RELATED APPLICATIONS

This application claims priority to U.S. Provisional Application No. 60/938,442 filed on May 16, 2007, and is hereby incorporated herein by reference in its entirety.

BACKGROUND

The subject matter herein generally relates to medical imaging, and more specifically, to a system and method to navigate a tool through an imaged subject.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Types of medical imaging systems, for example, computerized tomography (CT), magnetic resonance imaging (MRI), positron emission tomography (PET), ultrasound (US), radiological machines, etc., can be useful in providing static image guiding assistance to medical procedures. The above-described imaging systems can provide two-dimensional or three-dimensional images that can be displayed to provide a surgeon or clinician with an illustrative map to guide a tool (e.g., a catheter) through an area of interest of a patient's body.

When performing a medical procedure, it is desired to calibrate or align the acquired image data of the imaged subject with the tracked tool so as to navigate through the imaged subject. Yet, the sensors to the track the tool and the detectors to acquire the image data may not be precisely located due to manufacturing variation. One example of application of image-guided surgery is to perform an intervention procedure to treat cardiac disorders or arrhythmias. Heart rhythm disorders or cardiac arrhythmias are a major cause of mortality and morbidity. Atrial fibrillation is one of the most common sustained cardiac arrhythmia encountered in clinical practice. Cardiac electrophysiology has evolved into a clinical tool to diagnose these cardiac arrhythmias. As will be appreciated, during electrophysiological studies, probes, such as catheters, are positioned inside the anatomy, such as the heart, and electrical recordings are made from the different chambers of the heart.

A certain conventional image-guided surgery technique used in interventional procedures includes inserting a probe, such as an imaging catheter, into a vein, such as the femoral vein. The catheter is operable to acquire image data to monitor or treat the patient. Precise guidance of the imaging catheter from the point of entry and through the vascular structure of the patient to a desired anatomical location is progressively becoming more important. Current techniques typically employ fluoroscopic imaging to monitor and guide the imaging catheter within the vascular structure of the patient.

BRIEF SUMMARY

A technical effect of the embodiments of the system and method described herein includes increasing the field of view of image data acquisition employed to generate three- or four-dimensional reconstruction of images to guide an interventional surgery procedure. In general, as a surgeon moves the medical instrument with respect to the patient's anatomy, virtual images of the instrument or object are displayed simultaneously relative to real-time acquired image data represented in the model of the patient's anatomy. Another technical effect of the system and method described herein of tracking includes readily tracking the spatial relationship of the medical instruments or objects traveling through an operating space of patient. Yet, another technical effect of the system and method described herein includes reducing manpower, expense, and time to perform interventional procedures, thereby reducing health risks associated with long-term exposure of the subject to radiation.

According to one embodiment, a system operable to generate a four-dimensional (4D) model of an imaged anatomy, the system comprising a controller and an imaging system including an imaging probe in communication with the controller. The 4D imaging probe is operable to acquire a real-time, 3D image data relative to a direction of image acquisition along an imaging plane. The system further includes a tracking system in communication with the controller. The tracking system includes at least one tracking element integrated with the 4D ultrasound imaging probe. The system is operable to process the real-time, 3D image data acquired by the imaging probe relative to generally real-time tracking information acquired by the tracking system to generate a 4D model of the imaged anatomy.

According to another embodiment, a method of image acquisition of an imaged anatomy is provided. The method comprises the steps of acquiring a series of partial view 3D image data with a 4D imaging probe defined by an image coordinate system and a time reference; tracking a position of the 4D imaging probe relative to the time reference and a tracking coordinate system; generating a 4D model of the imaged anatomy by merging the series of partial view 3D image data defined relative to the time reference; and displaying the 4D model in superposition with a representation of the tracked position of the imaging probe.

Systems and methods of varying scope are described herein. In addition to the aspects of the subject matter described in this summary, further aspects of the subject matter will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
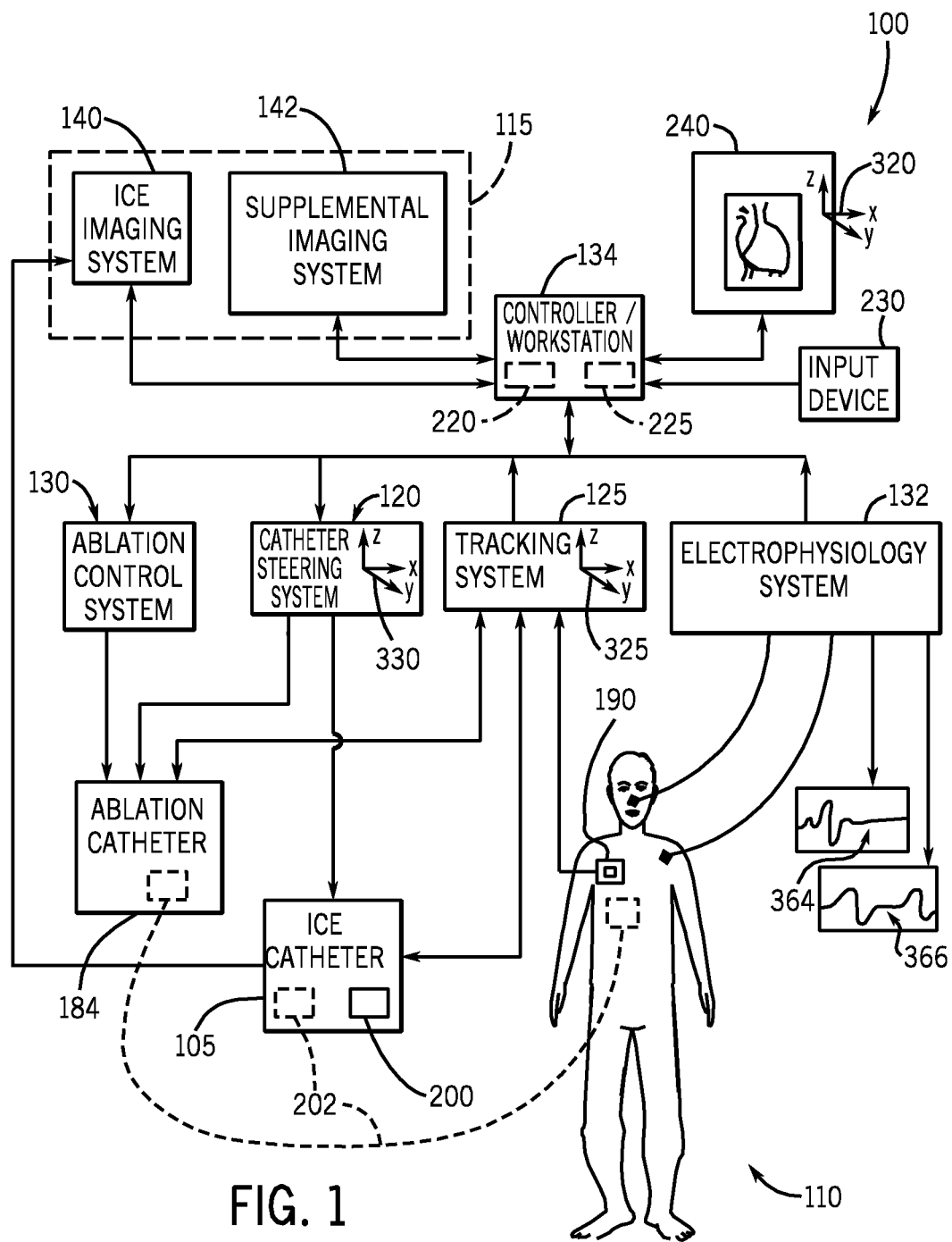
FIG. 1 illustrates a schematic diagram of an embodiment of a system of the subject matter described herein to perform imaged guided medical procedures on an imaged subject.

FIG. 1 generally illustrates an embodiment of a system 100 operable to create a full-view three- or four-dimensional (3D or 4D) image or model from a series of generally real-time, acquired 3D or 4D image data (e.g., ultrasound) relative to tracked position information of an imaging probe (e.g., catheter 105) traveling through the imaged subject 110. Although the following description is in regard to a catheter, the type of probe (e.g., endoscope, laparoscope, etc. or combination thereof) can vary. One embodiment of the system 100 is operable to acquire the series of 3D or 4D ultrasound image data while simultaneously rotating and tracking a position and orientation of the catheter 105 through the imaged subject. From the acquired 3D or 4D ultrasound image data, a technical effect of the system 100 includes creating an illustration of a full-view, 4D model of a region of interest (e.g., a beating heart) so as to guide delivery of an instrument.

An embodiment of the system 100 generally includes an image acquisition system 115, a steering system 120, a tracking system 125, an ablation system 130, and an electrophysiology system 132 (e.g., a cardiac monitor, respiratory monitor, pulse monitor, etc. or combination thereof), and a controller or workstation 134.

Still referring to FIG. 1, the image acquisition system 115 is generally operable to generate a three-dimensional, or four-dimensional image model corresponding to an area of interest of the imaged subject 110. Examples of the image acquisition system 115 can include, but are not limited to, computed tomography (CT), magnetic resonance imaging (MRI), x-ray or radiation, positron emission tomography (PET), ultrasound (US), angiographic, fluoroscopic, and the like or combination thereof. The image acquisition system 115 can be operable to generate static images acquired by static imaging detectors (e.g., CT systems, MRI systems, etc.) prior to a medical procedure, or real-time images acquired with real-time imaging detectors (e.g., angiographic systems, fluoroscopic systems, laparoscopic systems, endoscopic systems, etc.) during the medical procedure. Thus, the types of images acquired by the acquisition system 115 can be diagnostic or interventional.

An embodiment of the image acquisition system 115 includes a real-time, intracardiac echocardiography (ICE) imaging system 140 that employs ultrasound to acquire image data of the patient's anatomy and to merge acquired image data to generate a three-dimensional model of the patient's anatomy relative to time, generally herein referred to as a four-dimensional (4D) model or image. In accordance with another embodiment, the image acquisition system 115 is operable to fuse or combine acquired image data using above-described ICE imaging system 140 with pre-acquired or intra-operative image data or image models (e.g., two- or three-dimensional reconstructed image models) generated by another type of supplemental imaging system 142 (e.g., CT, MRI, PET, ultrasound, fluoroscopy, x-ray, etc. or combinations thereof).

Figure 2:
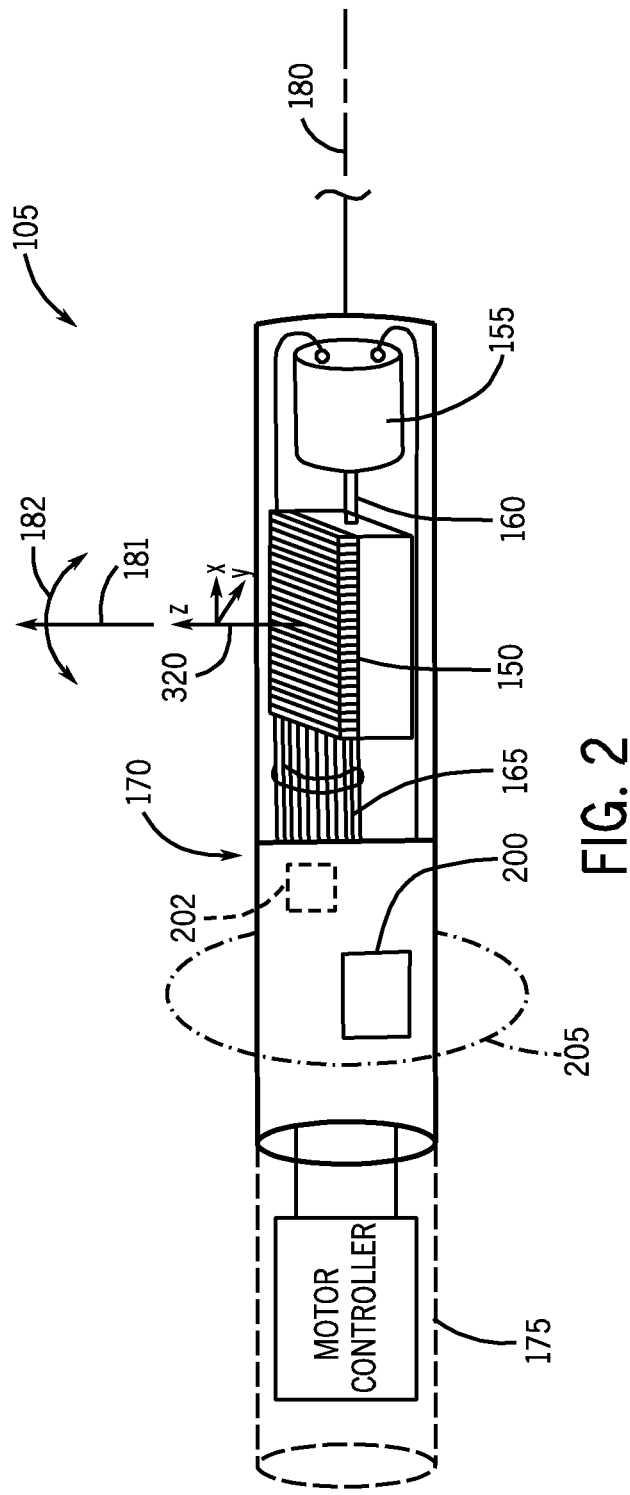
FIG. 2 illustrates a picture of a tool to travel through the imaged subject.

FIG. 2 illustrates one embodiment of the catheter 105, herein referred to as an ICE catheter 105. The illustrated embodiment of the ICE catheter 105 includes a transducer array 150, a micromotor 155, a drive shaft or other mechanical connection 160 between the micromotor 155 and the transducer array 150, an interconnect 165, and a catheter housing 170.

According to the illustrated embodiment in FIG. 2, the micromotor 155 via the drive shaft 160 generally rotates the transducer array 150. The rotational motion of the transducer array 150 is controlled by a motor control 175 of the micromotor 155. The interconnect 165 generally refers to, for example, cables and other connections coupling so as to receive and/or transmit signals between the transducer array 150 with the ICE imaging system (shown in FIG. 1) 105. An embodiment of the interconnect 165 is configured to reduce its respective torque load on the transducer array 150 and the micromotor 155.

An embodiment of the catheter housing 170 generally encloses the transducer array 150, the micromotor 155, the drive shaft 160, and the interconnect 165. The catheter housing 170 may further enclose the motor control 175 (illustrated in dashed line). The catheter housing is generally of a material, size, and shape adaptable to internal imaging applications and insertion into regions of interest of the imaged subject 110. At least a portion of the catheter housing 170 that intersects the ultrasound imaging volume or scanning direction is comprised of acoustically transparent (e.g., low attenuation and scattering, acoustic impedance near that of the blood and tissue ($Z\sim 1.5M$ Rayl)) material. An embodiment of the space between the transducer array 150 and the housing 170 is filled with acoustic coupling fluid (e.g., water) having an acoustic impedance and sound velocity near those of blood and tissue (e.g., $Z\sim 1.5M$ Rayl, $V\sim 1540$ m/sec).

An embodiment of the transducer array 150 is a 64-element one-dimensional array having 0.110 mm azimuth pitch, 2.5 mm elevation, and 6.5 MHz center frequency. The elements of the transducer array 150 are electronically phased in order to acquire a sector image generally parallel to a longitudinal axis 180 of the catheter housing 170. In operation, the micromotor 155 mechanically rotates the transducer array 150 about the longitudinal axis 180. The rotating transducer array 150 captures a plurality of two-dimensional images for transmission to the ICE imaging system 140 (shown in FIG. 1). The ICE imaging system 140 (See FIG. 1) is generally operable to assemble the sequence or succession of acquired 2D images so as to generally produce or generate 3D image or reconstructed models of the imaged subject 110.

Still referring to FIG. 2, the motor control 175 via the micromotor 155 generally regulates or controls the rate of rotation of the transducer array 150 about the longitudinal axis 180 of the ICE catheter 105. For example, the motor control 175 can instruct the micromotor 155 to rotate the transducer array 150 relatively slowly to produce the 3D reconstructed image or model. Also, the motor control 175 can instruct the micromotor 155 to rotate the transducer array 150 relatively faster to produce a real-time, 3D reconstructed image or model, referred to as the 4D reconstructed image or model. The 4D reconstructed image or model can be defined to include the 3D reconstructed image or model correlated relative to a general instant in time or instantaneous time. The motor control 175 is also generally operable to vary the direction of rotation so as to generally create an oscillatory motion of the transducer array 150. By varying the direction of rotation, the motor control 175 is operable to reduce the torque load associated with the interconnect 165, thereby enhancing the performance of the transducer array 150 to focus imaging on specific regions within the range of motion of the transducer array 150 about the longitudinal axis 180.

Referring back to FIG. 1, an embodiment of the steering system 120 is generally coupled in communication to control maneuvering (including the position or the orientation) of the ICE catheter 105. The embodiment of the system 100 can include synchronizing the steering system 120 with gated image acquisition by the ICE imaging system 140. The steering system 120 may be provided with a manual catheter steering function or an automatic catheter steering function or combination thereof. With selection of the manual steering function, a user manually aligns an imaging plane vector 181 (See FIG. 2) relative to a marker at the ICE catheter 105 shown on the 3D ICE reconstructed image or model, as well as directs the ICE catheter 105 to a target anatomical site. With selection of the automatic steering function, the controller 134 and/or steering system 120 or combination thereof estimates a displacement or a rotation angle 182 (See FIG. 2) relative to a reference (e.g., see ICE imaging reference frame discussed later) that is needed to aim the ICE imaging plane vector 181 (See FIG. 2) from the catheter 105, passes position information of the ICE catheter 105 to the steering system 120, and automatically drives or positions the ICE catheter 105 to continuously follow the delivery of a second instrument (e.g., an ablation catheter 184 of the ablation system 130). The reference can vary.

Figure 3:
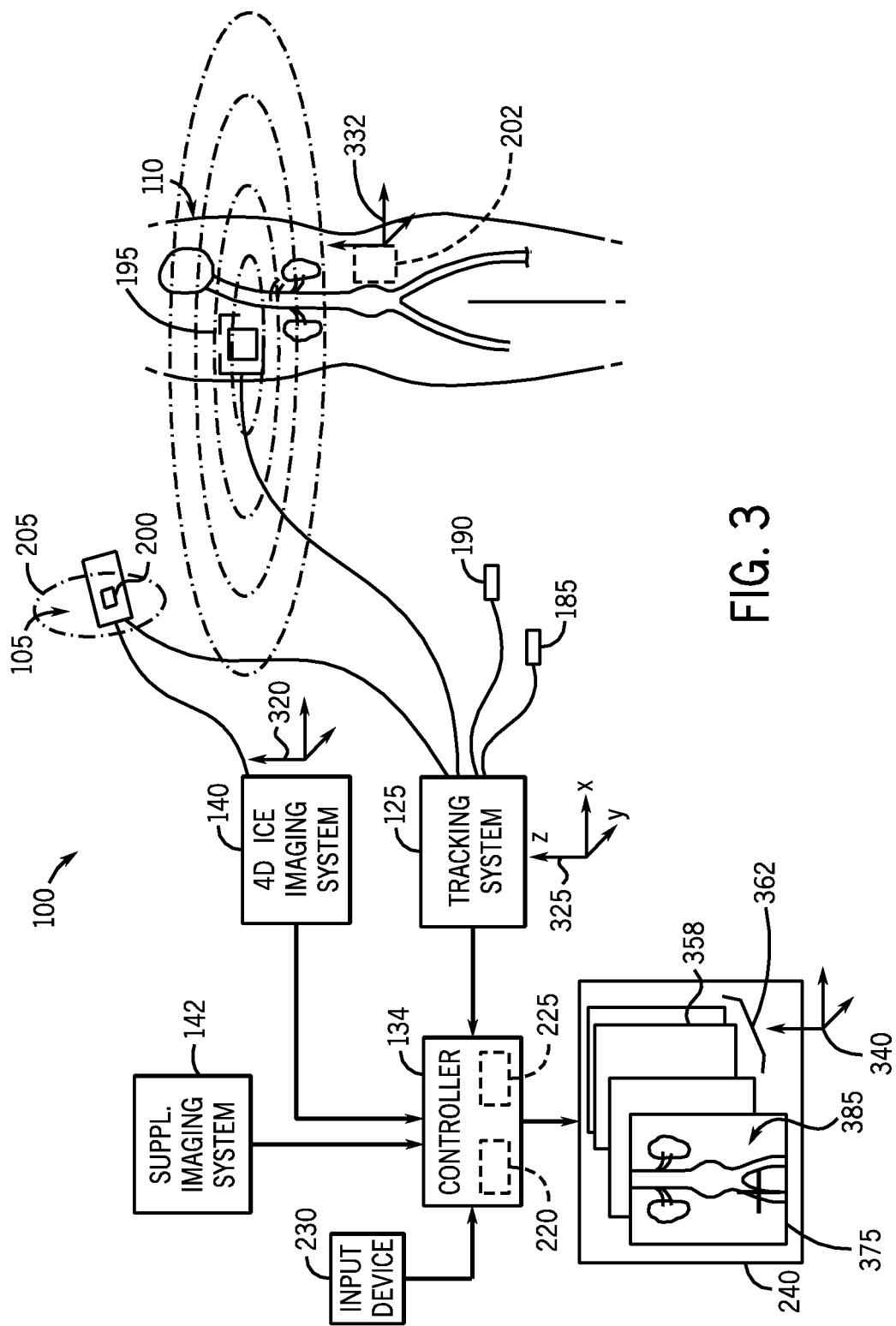
FIG. 3 illustrates a more detailed schematic diagram of a tracking system in combination with an imaging system as part of the system described in FIG. 1.

Referring to FIGS. 1 and 3, the tracking system 125 is generally operable to track or detect the position of the tool or ICE catheter 105 relative to the acquired image data or 3D or 4D reconstructed image or model generated by the image acquisition system 115, or relative to delivery of a second instrument or tool (e.g., ablation system 130, electrophysiology system 132).

As illustrated in FIG. 3, an embodiment of the tracking system 125 includes an array or series of microsensors or tracking elements 185, 190, 195, 200 connected (e.g., via a hard-wired or wireless connection) to communicate position data to the controller 134 (See FIG. 1). Yet, it should be understood that the number of tracking elements 185, 190, 195, 200 can vary. An embodiment of the system 100 includes intraoperative tracking and guidance in the delivery of the at least one catheter 184 of the ablation system 130 by employing a hybrid electromagnetic and ultrasound positioning technique. The hybrid electromagnetic/ultrasound positioning technique facilitates dynamic tracking by locating tracking elements or dynamic references 185, 190, 195, 200, alone or in combination with ultrasound markers 202 (e.g., comprised of metallic objects such brass balls, wire, etc.). The ultrasonic markers 202 may be active (e.g., illustrated in dashed line located at catheters 105 and 184) or passive targets (e.g., illustrated in dashed line at imaged anatomy of subject 110) (See FIG. 1). An embodiment of the ultrasound markers 202 can be located at the ICE catheter 105 and/or ablation catheter 184 (See FIG. 1) so as to be identified or detected in acquired image data by supplemental imaging system 142 and/or the ICE imaging system 140. The tracking system 125 can be configured to selectively switch between tracking relative to electromagnetic tracking elements 185, 190, 195, 200 or ultrasound markers 202 or simultaneously track both.

For sake of example and referring to FIG. 3, assume the series of tracking elements 185, 190, 195, 200 includes a combination of transmitters or dynamic references 185 and 190 in communication or coupled (e.g., RF signal, optically, electromagnetically, etc.) with one or more receivers 195 and 200. The number and type transmitters in combination with receivers can vary. Either the transmitters 185 and 190 or the receivers 195 and 200 can define the reference of the spatial relation of the tracking elements 185, 190, 195, 200 relative to one another. An embodiment of one of the receivers 195 represents a dynamic reference at the imaged anatomy of the subject 110. An embodiment of the system 100 (See FIG. 1) can be operable to register or calibrate the location (e.g., position and/or orientation) of the tracking elements 185, 190, 195, 200 relative to the acquired imaging data by the image acquisition system 115 (See FIG. 1), and operable to generate a graphic representation suitable to visualize the location of the tracking elements 185, 190, 195, 200 relative to the acquired image data.

The tracking elements 185, 190, 195, 200 generally enable a surgeon to continually track the position and orientation of the catheters 105 or 184 (See FIG. 1) during surgery. The tracking elements 185, 190, 195, 200 may be passively powered, powered by an external power source, or powered by an internal battery. One embodiment of one or more of the tracking elements or microsensors 185, 190, 195, 200 include electromagnetic (EM) field generators having microcoils operable to generate a magnetic field, and one or more of the tracking elements 185, 190, 195, 200 include an EM field sensor operable to detect an EM field. For example, assume tracking elements 185 and 190 include a EM field sensor operable such that when positioned into proximity within the EM field generated by the other tracking elements 195 or 200 is operable to calculate or measure the position and orientation of the tracking elements 195 or 200 in real-time (e.g., continuously), or vice versa, calculate the position and orientation of the tracking elements 185 or 190.

For example, tracking elements 185 and 190 can include EM field generators attached to the subject 110 and operable to generate an EM field, and assume that tracking element 195 or 200 includes an EM sensor or array operable in combination with the EM generators 185 and 190 to generate tracking data of the tracking elements 185, 190 attached to the patient 110 relative to the microsensor 195 or 200 in real-time (e.g., continuously). According to one embodiment of the series of tracking elements 185, 190, 195, 200, one is an EM field receiver and a remainder are EM field generators. The EM field receiver may include an array having at least one coil or at least one coil pair and electronics for digitizing magnetic field measurements detected by the receiver array. It should, however, be understood that according to alternate embodiments, the number and combination of EM field receivers and EM field generators can vary.

The field measurements generated or tracked by the tracking elements 185, 190, 195, 200 can be used to calculate the position and orientation of one another and attached instruments (e.g., catheters 105 or 184 (See FIG. 1)) according to any suitable method or technique. In one embodiment, the field measurements tracked by the combination of tracking elements 185, 190, 195, 200 can be digitized into signals for transmission (e.g., wireless, or wired) to the tracking system 125 or controller 134. The controller 134 is generally operable to register the position and orientation information of the one or more tracking elements 185, 190, 195, 200 relative to the acquired imaging data from ICE imaging system 140 or other supplemental imaging system 142. Thereby, the system 100 is operable to visualize or illustrate the location of the one or more tracking elements 185, 190, 195, 200 or attached catheters 105 or 184 (See FIG. 1) relative to pre-acquired image data or real-time image data acquired by the image acquisition system 115 (See FIG. 1).

Referring now to FIGS. 2 and 3, an embodiment of the tracking system 125 includes the tracking element 200 located at the ICE catheter 105. The tracking element 200 is in communication with the receiver 195. This embodiment of the tracking element 200 includes a transmitter that comprises a series of coils that define the orientation or alignment of the ICE catheter 105 about the rotational axis (generally aligned along the longitudinal axis 180) of the ICE catheter 105. The tracking element 200 can be located integrally with the ICE catheter 105 and can be generally operable to generate or transmit a magnetic field 205 to be detected by the receiver 195 of the tracking system 125. In response to passing through the magnetic field 205, the receiver 195 generates a signal representative of a spatial relation and orientation of the receiver 195 or other reference relative to the transmitter 200. Yet, it should be understood that the type or mode of coupling, link or communication (e.g., RF signal, infrared light, magnetic field, electrical potential, etc.) operable to measure the spatial relation varies. The spatial relation and orientation of the tracking element 200 is mechanically predefined or measured in relation relative to a feature (e.g., a tip) of the ICE catheter 105. Thereby, the tracking system 125 is operable to track the position and orientation of the ICE catheter 105 navigating through the imaged subject 110.

Alternatively, the tracking elements 185, 190, or 200 can include a plurality of coils (e.g., Hemholtz coils) operable to generate a magnetic gradient field to be detected by the receiver 195 of the tracking system 125 and which defines an orientation of the ICE catheter 105. An embodiment of the receiver 195 includes at least one conductive loop operable to generate an electric signal indicative of spatial relation and orientation relative to the magnetic field generated by the tracking elements 185, 190 and 200.

Referring back to FIG. 1, an embodiment of the ablation system 130 includes the ablation catheter 184 that is operable to work in combination with the ICE catheter 105 of the ICE imaging system 140 to deliver ablation energy to ablate or end electrical activity of tissue of the imaged subject 110. An embodiment of the ICE catheter 105 can include or be integrated with the ablation catheter 184 or be independent thereof. An embodiment of the ablation catheter 184 can include one of the tracking elements 185, 190 of the tracking system 125 described above to track or guide intra-operative delivery of ablation energy to the imaged subject 110. Alternatively or in addition, the ablation catheter 184 can include ultrasound markers 202 operable to be detected from the acquired ultrasound image data generated by the ICE imaging system 140. The ablation system 130 is generally operable to manage the ablation energy delivery to an ablation catheter 184 relative to the acquired image data and tracked position data.

Still referring to FIG. 1, an embodiment of an electrophysiological system(s) 132 is connected in communication with the ICE imaging system 140, and is generally operable to track or monitor or acquire data of the cardiac cycle or respiratory cycle of imaged subject 110. Data acquisition can be correlated to the gated acquisition or otherwise acquired image data, or correlated relative to generated 3D or 4D models created by the image acquisition system 115.

An embodiment of the controller or workstation computer 134 can be generally connected in communication with and controls the image acquisition system 115 (e.g., the ICE imaging system 140 or supplemental imaging system 142), the steering system 120, the tracking system 125, the ablation system 130, and the electrophysiology system 132 so as to enable each to be in synchronization with one another and to enable the data acquired therefrom to produce or generate a full-view 3D or 4D ICE model of the imaged anatomy.

An embodiment of the controller 134 includes a processor 220 in communication with a memory 225. The processor 220 can be arranged independent of or integrated with the memory 225. Although the processor 220 and memory 225 are described located at the controller 134, it should be understood that the processor 220 or memory 225 or portion thereof can be located at the image acquisition system 115, the steering system 120, the tracking system 125, the ablation system 130 or the electrophysiology system 132 or combination thereof.

The processor 220 is generally operable to execute the program instructions representative of acts or steps described herein and stored in the memory 225. The processor 220 can also be capable of receiving input data or information or communicating output data. Examples of the processor 220 can include a central processing unit of a desktop computer, a microprocessor, a microcontroller, or programmable logic controller (PLC), or the like or combination thereof.

An embodiment of the memory 225 generally comprises one or more computer-readable media operable to store a plurality of computer-readable program instructions for execution by the processor 220. The memory 225 can also be operable to store data generated or received by the controller 134. By way of example, such media may comprise RAM, ROM, PROM, EPROM, EEPROM, Flash, CD-ROM, DVD, or other known computer-readable media or combinations thereof which can be used to carry or store desired program code in the form of instructions or data structures and which can be accessed by a general purpose or special purpose computer or other machine with a processor. When information is transferred or provided over a network or another communications connection (either hardwired, wireless, or a combination of hardwired or wireless) to a machine or remote computer, the remote computer properly views the connection as a computer-readable medium. Thus, any such a connection is properly termed a computer-readable medium.

As shown in FIG. 1, the controller 134 further includes or is in communication with an input device 230 and an output device 240. The input device 230 can be generally operable to receive and communicate information or data from a user to the controller 210. The input device 230 can include a mouse device, pointer, keyboard, touch screen, microphone, or other like device or combination thereof capable of receiving a user directive. The output device 240 is generally operable to illustrate output data for viewing by the user. An embodiment of the output device 240 can be operable to simultaneously illustrate or fuse static or real-time image data generated by the image acquisition system 115 (e.g., the ICE imaging system 140 or supplemental imaging system 142) with tracking data generated by the tracking system 125. The output device 240 is capable of illustrating two-dimensional, three-dimensional, and/or four-dimensional image data or combinations thereof through shading, coloring, and/or the like. Examples of the output device 240 include a cathode ray monitor, a liquid crystal display (LCD) monitor, a touch-screen monitor, a plasma monitor, or the like or combination thereof.

Figure 4:
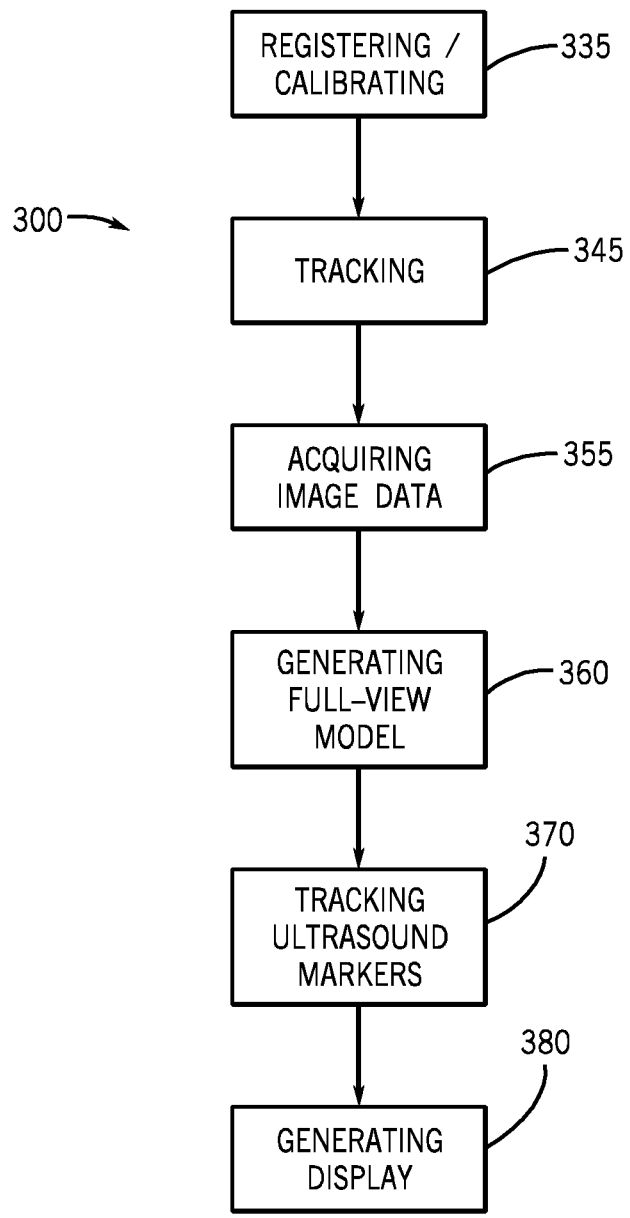
FIG. 4 shows an embodiment of a method of performing an image-guided procedure via the system of FIG. 1.

Having provided a description of the general construction of the system 100, the following is a description of a method 300 (see FIG. 4) of operation of the system 100 in relation to the imaged subject 110. Although an exemplary embodiment of the method 300 is discussed below, it should be understood that one or more acts or steps comprising the method 300 could be omitted or added. It should also be understood that one or more of the acts can be performed simultaneously or at least substantially simultaneously, and the sequence of the acts can vary. Furthermore, it is embodied that at least several of the following steps or acts can be represented as a series of computer-readable program instructions to be stored in the memory 225 of the controller 210 for execution by the processor 220 or one or more of the image acquisition system 115, the steering system 120, the tracking system 125, or the ablation system 130 or the remote computer station connected thereto via a network (wireless or wired).

Referring now to FIGS. 1 and 3 and for sake of example, assume that the spatial relation and orientation of the image data acquired by the transducer array 150 of the ICE imaging system 140 is defined by an image coordinate system 320 referenced in predetermined spatial relation and orientation relative to the transducer array 150 (See FIG. 2) at the ICE catheter 105. The image coordinate system 320 generally defines the spatial relation of voxels or pixels of image data relative to one another in the generated image frames or models generated by the ICE imaging system 140 in three-dimensions relative to time (i.e., four-dimensional model). Also, for sake of example, assume the tracking system 125 utilizes a tracking coordinate system 325 to define tracking spatial relation and orientation and movement of the tracking elements 185, 190, 195, and 200 or respective catheters 105 and 184 relative to one another and to time. For example, the tracking coordinate system 325 references the orientation and spatial relation of the tracking element 200 at the ICE catheter 105 relative to one of the receiver or references 185, 190, 195 of the tracking system 125. Also, for sake of example, assume the steering system 130 utilizes a mechanical or steering coordinate system 330 to define maneuvering and orientation of either or both of the catheters 105 and 184 relative to one another. The tracking system 125 may further employ an ultrasonic coordinate system 332 defined by ultrasonic markers 202. Although these coordinate systems 320 and 325 and 330 can be described as Cartesian x-y-z coordinate systems, the type of coordinate systems 320, 325, 330, 332 (e.g., polar, etc.) can vary. In addition, the location and orientation of the coordinate systems 320, 325, 330, 332 can vary.

The controller 134 via the tracking system 125 is operable to track movement of the ICE catheter 105 in accordance with known mathematical algorithms programmed as program instructions of software for execution by the processor 220 of the controller 134 or by the tracking system 125. An exemplary navigation software is INSTATRAK® as manufactured by the GENERAL ELECTRIC® Corporation, NAVIVISION® as manufactured by SIEMENS®, and BRAINLAB®.

Referring back to FIG. 1, having described registration of the ICE imaging system 140 with the tracking system 125, the step of registering can further extend to registering the ICE imaging system 140 and tracking system 125 relative to other components of the system 100, including the steering system 120, ablation system 130, or the electrophysiological system(s) (e.g., cardiac monitoring system, respiratory monitoring system, etc.) 132, generally similar to the method of registering described above directed to the ICE imaging system 140 with the tracking system 125.

Referring to FIGS. 1 through 4, the method 300 includes a step 335 of registering and/or calibrating the image acquisition system 115 (including the ICE imaging system 140), the steering system 120, the tracking system 125, and the ablation system 130 with one another. An embodiment of the step 335 of calibrating and registering includes registering both an ICE imaging reference frame or ICE imaging catheter coordinate system (referred to later as "ice") 320 relative to the mechanical reference frame or coordinate system 330 of the steering system (referred to later as "mcs") 130, and additionally registering the previous coordinate systems 320, 330 relative to the electromagnetic microsensor or dynamic reference sensor frame or coordinate system (referred to later as "scs") 325. The above described registering events or coordinate transformations can be denoted as T(ice->scs) and T(mcs->scs), respectively.

An embodiment of the registering and/or calibrating step 335 includes the step of rigidly attaching at least one dynamic reference microsensor or tracking element 185, 190, 195 or 200 (See FIG. 2) at the imaged anatomy. An example of this step includes integrating the dynamic reference microsensor at the distal end of a (steerable) catheter (e.g., dynamic reference catheter) 105 (See FIG. 2), and delivering and anchoring the at least one dynamic reference tracking element 185, 190, 195, or 200 (See FIG. 2) at the imaged organ, e.g. the heart. According to another embodiment, the dynamic reference can be independent and separate of the catheter 105.

The dynamic reference microsensor 185, 190, 195, or 200 establishes a so-called world coordinate system (world reference frame-dynamic reference microsensor) (wcs) 340 (See FIG. 3) that enables the system 100 to compensate for the respiratory and/or cardiac motion of the imaged organ in the display of the acquired generally real-time, 3D ultrasound image data or pre-operative or intra-operative image data acquired by the supplemental imaging system 142. According to another example, the dynamic reference microsensor can be rigidly attached externally of the imaged subject 110, e.g. the patient's chest such that the system 100 can compensate for motion of the imaged organ via synchronizing image acquisition relative to the respiratory and/or cardiac cycle of the imaged subject 110 tracked by the electrophysiology system 132. The coordinate transformation from the tracking coordinate system 325 to the world coordinate system 340 can be denoted T(scs->wcs).

The embodiment of the method 300 further includes a step 345 of tracking (e.g., via the tracking system) a position or location of the at least one catheter 105 or 184 relative to the acquired image data. According to one embodiment of the method 300, at least one instrument catheter 105 or 184 is integrated with a plurality of hybrid electromagnetic position microsensors 185, 190, 195, 200 and ultrasonic markers 202. The electromagnetic microsensors 185, 190, 195, 200 and ultrasonic markers 202 can both be located and rigidly mounted on the at least one instrument catheter 105 or 184. A computer image-processing program is operable to detect and mark positions of the ultrasonic markers 202 relative to the generated 3D or 4D ICE image model.

The controller 134 can be generally operable to align positions of the ultrasonic markers 202 with the tracking coordinate reference frame or coordinate system 325. This registration information may be used for the alignment (calibration) between the tracking reference frame or coordinate system 325 and the ultrasonic marker reference frame or coordinate system 332 relative to the ICE imaging reference frame or coordinate system 320. This information may also be used for detecting the presence of electromagnetic distortion or tracking inaccuracy.

An embodiment of the method 300 further includes a step 355 of acquiring image data (e.g., scan) of the anatomy of interest of the imaged subject 110. An embodiment of the step of acquiring image data includes generating a series of partial-views 358 of 3D or 4D image data from real-time image data acquired while rotating the ICE catheter 105 around the longitudinal axis 180 (See FIG. 2) that extends through the center of the ICE catheter 105. Image acquisition with the catheter 105 can include more general motion in addition to rotation of the transducer array 150 about axis 180. The motor 155 can provide some range of rotation of the transducer array 150 to generate a 4D model 112 with an enhanced field of view. To image an entire "anatomy of interest" (e.g. an entire chamber of the heart), the imaging catheter 105 can be deflected, advanced, or retracted in addition to rotation of the transducer array 150.

An embodiment of the image acquisition step 355 includes calculating positions or degree of rotation of the ICE catheter 105 about the longitudinal axis 180. The image acquisition step 355 can further include synchronizing or gating a sequence of image acquisition relative to tracking data acquired by the hybrid tracking system 125 (e.g., tracking a location (e.g., position and/or orientation) relative to the acquired image data). In addition, the image acquisition step 355 can further include synchronizing or gating a sequence of image acquisition relative to measuring cardiac and respiratory signals by the electrophysiology system 132.

According to one embodiment of the image acquisition step 355, the ablation catheter 184 can be detected or is visible in the acquired image data by the ICE imaging system 140. By "scribbling" the anatomical surface of the anatomy of interest with the at least one instrument catheter 184 relative to acquired tracking data of the location of the catheters 105 or 184, the anatomical boundary may be enhanced to result in a more accurate surface model for image registration and surgical planning.

Referring to FIGS. 1 through 4, an embodiment of the method 300 further includes a step 360 of generating or reconstructing a full-view 3D or 4D model 362 from the sequence of generated partial-view 3D or 4D image views 358 relative to the world coordinate frame 340 established by the dynamic reference or tracking element 185, 190, 195, or 200. The 4D ICE imaging system 140, the tracking system 125, the steering system 120, the cardiac and respiratory monitoring system 132, and the 4D ICE imaging catheter 105 are generally involved in acquisition and reconstructing the full view 4D ICE model for the anatomy of the imaged subject 110. The step 360 can include merging the series of partial 3D or 4D image views or views 358 (See FIG. 3) relative to acquired electrophysiology data (e.g., cardiac cycle, respiratory cycle) acquired by the electrophysiology system 132. The step 360 can further include generating a display of the generated 3D or 4D model 362 (See FIG. 3) synchronized relative to electrophysiology signals 364, 366 (see FIG. 1).

An embodiment of the method 300 can further include a step 370 of acquiring or measuring location data of the ultrasonic markers 202 described above by detecting or identifying the voxels illustrative thereof in the acquired, real-time 3D or 4D ultrasound image data via the ICE imaging system 140. An embodiment of the ultrasonic markers 202 can be configured to identify each of a series of tools or catheters 105 or 184 delivered through an imaged subject 110. An embodiment of the pattern of the tracking elements 185, 190, 195, 200 and/or ultrasonic markers 202 may be uniquely defined for different types of instrument catheters 105 or 184 for identification purposes. Dependent on the uniquely defined tracking elements 185, 190, 195, 200 and/or ultrasonic markers 202, the image acquisition system 115, tracking system 125 or controller 134 or combination thereof can be operable to uniquely identify location and orientation of each of the tools or catheters 105 and 184. An embodiment of the system 100 is operable to extract the location of voxels from the acquired image data correlated to the imaging of the ultrasonic markers 202. In this way, the location of the ultrasonic markers 202 may be tracked with respect to the ICE catheter 105 or ablation catheter 184, or vice versa.

An embodiment of the system 100 includes a software having image processing programs operable to extract the locations of the ultrasonic markers 202 from the acquired generally real-time, 3D or 4D ultrasound image data (e.g., partial views 358), an electromagnetic distortion detection program using information from the 3D or 4D ultrasound image data, and the tracking program with instructions to execute steps of the hybrid tracking technique described above. According to one embodiment, the system 100 processes acquired 3D or 4D ICE image data to extract voxel positions of the ultrasonic markers 202 relative to the ablation catheter 184. The system 100 also processes the acquired 3D or 4D ultrasound image data to generate a surface model of the imaged anatomy. The system 100 is also operable to calculate the vector 181 generally representative of a central direction of a field of view of the ICE imaging system 140.

Referring to FIGS. 1 through 5, according to another embodiment, the system 100 includes a graphic user interface (GUI) 371 operable to facilitate image data acquisition and reconstruction of the 3D or 4D ICE model 362, including display of a generally real-time 3D or 4D ICE image model 362 created from the acquired anatomical data; to display detected/identified locations or representations thereof of at least one instrument catheter 105 or 184 relative to the illustrated, real-time 3D or 4D ICE image model 362; to display the vector 181 showing the general central direction of a field of view of the 3D or 4D ICE image model 362; to receive an input of a selection of a target anatomical site relative to the 3D or 4D ICE image model 362; to display a distance between the tip of the catheter 105 or 184 relative to an anatomical surface of the 3D or 4D ICE image model 362; to display a path of delivery of the catheter 105 or 184 relative to a target anatomical site illustrated at the 3D or 4D ICE image model 362; to display synchronization of image data acquisition to create the 3D or 4D ICE image model 362 relative to the signal of the tracked cardiac or respiratory cycle; and to receive input indicative of a selection between a manual and automatic steering function of the ICE catheter 105.

According to one embodiment, the system 100 automatically conducts a 4D scan of the anatomy of interest of the imaged subject 110. The controller 134 can calculate or estimate a number of the ICE scans needed to generate the full-view 4D model reconstruction. Based on the field of view (FOV) of the ultrasound transducer array 150 and a tracked starting position of the ICE catheter 105, the system 100 is operable to calculate a set of orientations (e.g. T(mcs.p1->scs)T(scs->wcs), T(mcs.p2->scs)T(scs->wcs), . . . , T(mcs.pn->scs)T(scs->wcs) where p1, p2, and pn are different catheter orientations) of the ultrasound imaging plane 181 to conduct a full-view 4D scan in the dynamic reference sensor frame 340. The controller 134 can also communicate signals representative of instructions to the steering system 130 that direct automatic maneuvering and rotating of the ICE catheter 105 to a series of imaging positions, e.g., T(mcs.p1->scs)T(scs->wcs), T(mcs.p2->scs)T(scs->wcs), . . . , and T(mcs.pn->scs)T(scs->wcs).

Figure 5:
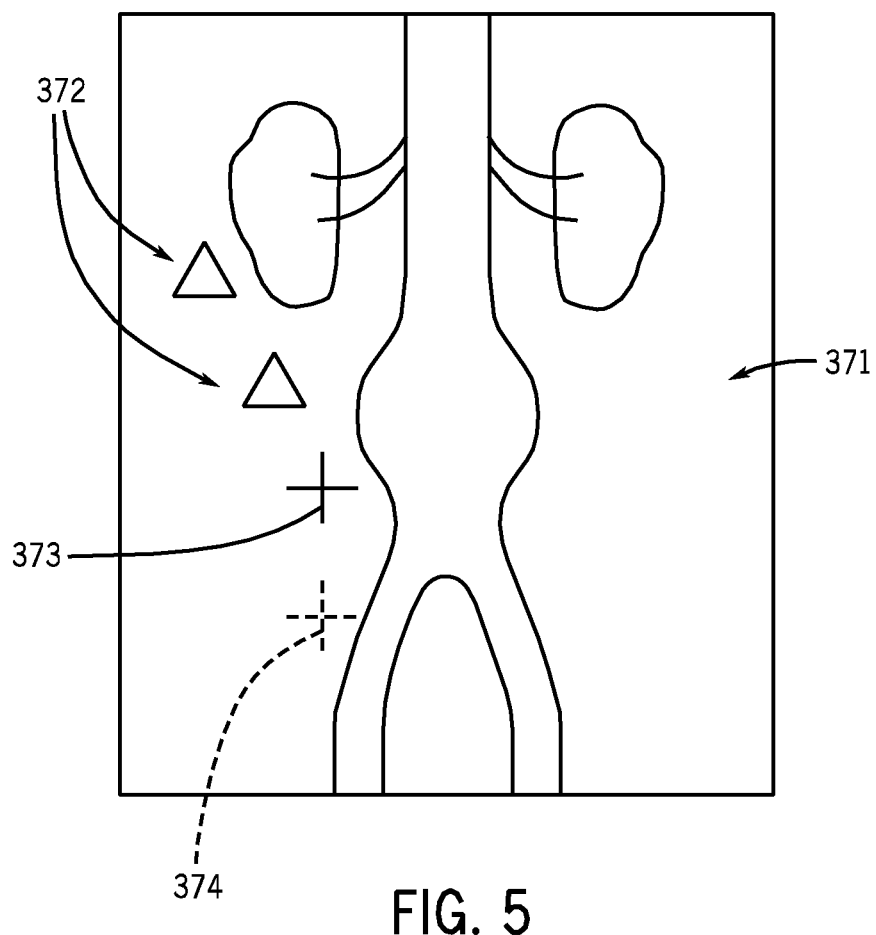
FIG. 5 shows an embodiment of an illustration of tracking historical, current, and future locations of diagnostic or therapeutic catheters via the system of FIG. 1 to form a surgical plan.

According to another embodiment, the ICE catheter 105 of the ICE imaging system 140 executes the full-view 3D or 4D ICE scan of the imaged anatomy according to received input instructions directed to manually drive the ICE catheter 105 into a series of imaging positions, as well as received input instructions directed to manually activate each event of image acquisition. Referring to FIG. 5, an embodiment of the GUI 371 facilitates the 3D or 4D ICE image acquisition via displaying representations 372 of a history of each position of the ICE catheter 105 or ablation catheter 184 at events of image acquisition, displaying a representation 373 of a current position of the ICE catheter 105, and displaying a representation 374 of a next or future position or location of an image acquisition event by the ICE catheter 105.

The 3D or 4D ICE image and catheter position acquisitions can be triggered at the preset cardiac and respiratory phase, e.g. t1, t2, . . . , tn. At a given catheter orientation (pi), the system 100 is operable to acquire and transform a series of ultrasound images relative to the world coordinate frame 340, represented by [T(ice.pi->scs)T(scs->wcs)].t1, [T(ice.pi->scs)T(scs->wcs)].t2, . . . , and [T(mcs.pi->scs)T(ice->wcs)].tn.

Alternatively, the 3D or 4D ICE image acquisition may be conducted at a dynamic or variable rate optimized according to the imaged volume, desired ultrasound image quality, etc. With each acquired ultrasound image volume (or plane or beam), the system 100 records a current cardiac and respiratory phase (ti), and the current catheter or image position (pi).

Upon the completion of the full-view 3D or 4D scan, the system 100 can reconstruct the generated series of partial views 358 of 3D or 4D ultrasound image data at different catheter orientations and different cardiac cycle time or phase. By transforming or registering the partial views 358 of the acquired 3D or 4D ICE image data relative to the world coordinate frame 340 (see FIG. 3), the system 100 can calculate the following transformations: [T(ice.p1->scs)T(scs->wcs)].t1, [T(ice.p1->scs)T(scs->wcs)].t2, [T(ice.p2->scs)T(scs->wcs)].t1, . . . , and [T(ice.pn->scs)T(scs->wcs)].tn.

To generate the full-view 3D or 4D ICE model 362, an embodiment of the system 100 can group the partial views 358 of 3D or 4D ultrasound image data according the cardiac timing sequence, e.g. [T(ice.p1->scs)T(scs->wcs)].t1, [T(ice.p2->scs)T(scs->wcs)].t1, . . . , and [T(ice.pn->scs)T(scs->wcs)].t1 at cardiac phase t1. A number of image processing techniques such as image smoothing, filtering, or averaging can be used to merge the series of partial views 358 to a full-view 3D or 4D ICE model 362 [T(ice.3D->wcs)].t1 for the t1 cardiac phase or the respiratory phase.

The controller 134 is operable to repeat the above-described image reconstruction process to create a full-view 3D or 4D ICE model of the anatomic structure, denoted as [T(ice.3D->wcs)].t1, [T(ice.3D->wcs)].t2, . . . , and [T(ice.3D->wcs)].tn, for the rest of the cardiac phases or respiratory phases.

According to one embodiment of the system 100 and method 300 described herein, the controller 134 can control operation of the steering system 120, the tracking system 125, the ablation system 130, and the electrophysiology monitoring system 132, the ICE imaging system 140 and/or any supplemental imaging system 142. Via the controller 134, the system 100 is operable to process the acquired image data relative to the acquired real-time tracking information from the hybrid tracking system 125 and the cardiac and respiratory cycle information from the electrophysiology system 132. The system 100 is further operable to generate full-view 3D or 4D ICE model of the imaged anatomy, register the acquired partial views 358 of the real-time 3D or 4D ICE image data with the generated full-view 3D or 4D model 362 or other pre-operative or intra-operative real-time non-ICE images 375 (e.g., MRI, CT, PET, etc.), and control the steering system 120 in maneuvering the ICE catheter 105 or ablation catheter 184 relative to the direction of the 3D or 4D ICE imaging plane 181 (or vice versa) (See FIG. 2).

Referring to FIGS. 1 through 5, the method 300 further includes a step 380 of generating a display 385 of the partial views 358 (See FIG. 3) of the general real-time 3D or 4D ICE image data superimposed or combined relative to one or more of the following: the full-view 4D ICE model 362 (See FIG. 3); one or more of an MRI, CT, PET, or other pre- or intra-operative images 375; representations 372, 373, 374 (See FIG. 5) of the generally real-time tracked positions of the ICE catheter 105 or therapy catheter 184 (See FIG. 1); the cardiac and/or respiratory cycle data 364, 366 (See FIG. 1) synchronized with a time of acquisition of the partial views 358 of the 3D or 4D ICE image data and positions of either catheter 105 or 184; a preoperative surgical plan, including identifying and illustrating the surgical or ablation targets according to preoperative or intraoperative images 375 (e.g., EP information superimposed on the full-view 3D or 4D model 362) (See FIG. 3); selection between manual and automatic catheter steering functions; and generating a display of the one or more locations of the surgical site on the full-view 3D or 4D ICE model 362 during delivery of the surgical treatment.

A technical effect of the embodiments of the system 100 and method 300 described above is to provide an image reconstruction algorithm that provides a full-view 4D image model of anatomic structure, fast registration of the acquired partial views 358 of the 3D or 4D ICE image data relative to other preoperative and intraoperative images 375, capability to create the surgical plan that comprises graphic representations of historical locations, current locations, and future locations of image acquisition 372, 373, 374 (See FIG. 5), and intra-operative guidance to maneuver various devices, for example the diagnostic or therapeutic catheters 105 or 184. The system 100 and method 300 also provide an integrated solution to create a full-view 3D or 4D ICE model 362 from the series of real-time partial 3D or 4D views 358 and catheter position information.

Another technical effect of the above-described system 100 and method 300 described above is an ability to register the 3D or 4D ICE imaging system 140 with the tracking system 125 or another type or supplemental imaging system 142 via execution of computer-readable program instructions stored and executable at the controller 134. As described above, the controller 134 is operable to perform registration of the coordinate systems 320, 325, 330, 332, 340 relative to one another.

Another technical effect of the system 100 and method 300 described above is an ability to combine image data and models generated by the ICE imaging system 140 with a location of the ICE catheter 105 or ablation catheter 184 being tracked by tracking system 125, all in combination with imaged data or models generated by another imaging system 142, with an ability to compensate for deficiencies in the imaged data acquired with the ICE imaging system 140. Accordingly, the system 100 and method 300 enhance tracking and guidance of the position and orientation of the catheter 105 or transducer array 150 navigating through the imaged subject 110. The system 100 and method 300 also synchronize tracking and guidance of movement and orientation of the ICE catheter 105 or ablation catheter 184 associated with the ablation system 130, with each other as well as with electrophysiological signals (e.g., respiratory cycle, cardiac cycle, etc.) as tracked by the electrophysiological system(s) 132.

Technical effects of integrating the 4D ICE imaging system 140 with the tracking system 125 includes, inter alia, enhancement of the field of the view of the 4D ICE imaging catheter 105, acceleration of the 4D ICE registration process with other pre-operative and intra-operative images, and enhancement of pre-operative surgical planning and intraoperative instrument catheter guidance.

Embodiments of the subject matter described herein include method steps which can be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of computer program code for executing steps of the methods disclosed herein. The particular sequence of such computer- or processor-executable instructions or associated structures represent examples of corresponding acts for implementing the functions described in such steps.

Embodiments of the subject matter described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the subject matter described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

This written description uses examples to disclose the subject matter, including the best mode, and also to enable any person skilled in the art to make and use the subject matter described herein. Accordingly, the foregoing description has been presented for purposes of illustration and description, and is not intended to be exhaustive or to limit the subject matter to the precise form disclosed, and modifications and variations are possible in light of the above teachings or may be acquired from practice of the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A tracking system comprising:
an imaging probe configured to travel through an imaged anatomy, the imaging probe operable to acquire real-time, three-dimensional (3D), image data of an imaged anatomy, the imaging probe configured to provide the 3D image data to an imaging system;
an input configured to receive, from the imaging system, a 3D model of a portion of the imaged anatomy, the 3D model being generated based on the 3D image data;
a tracking module including an electromagnetic tracking element integrated with the imaging probe to obtain real-time tracking information representative of a position of the imaging probe, the tracking module configured to selectively track the imaging probe using the tracking information;
an electrophysiology (EP) input configured to receive electroanatomical information from an EP system; and
a registration module configured to map the electroanatomical information onto the 3D model based on the tracking information to form a color-coded map of the portion of the imaged anatomy.

2. The system of claim 1, wherein the tracking module is further operable to automatically register and display newly acquired real-time, 3D image data, and real-time motion information on a 4D model.

3. The system of claim 1, wherein the EP system is operable to acquire a cardiac cycle and a respiratory cycle information in synchronization with a time of acquisition of the 3D image data, display the newly acquired, real-time, 3D image data superimposed onto a 4D model, the position of the imaging probe, and the cardiac and respiratory cycle information illustrated at a time of acquisition in synchronization relative to the time of acquisition of the newly acquired, real-time, 3D image data.

4. The system of claim 1, wherein the an electromagnetic tracking element comprises a receiver located at the imaged anatomy.

5. The system of claim 1, wherein a spatial relation and an orientation of the real-time 3D image data is defined by an image coordinate system referenced in a predetermined spatial relation and orientation relative to the imaging probe, wherein the spatial relation of the electromagnetic tracking element integrated with the imaging probe relative to a dynamic reference located at the imaged anatomy is defined by a tracking coordinate system.

6. The system of claim 1, wherein the 3D image data is acquired while rotating the imaging probe about a longitudinal axis that extends through a center of the imaging probe.

7. The system of claim 1, further comprising an ablation system having an ablation catheter in communication with the controller, the ablation catheter and the imaging probe both maneuvered by a steering system, wherein maneuvering of the imaging probe and the ablation catheter by the steering system is defined relative to a mechanical coordinate system registered in relation to an image coordinate system and a tracking coordinate system.

8. The system of claim 1, further comprising a controller configured to calculate a degree of rotation of a motor to drive movement of the imaging probe about a longitudinal axis of the imaging probe in synchronization relative to time of image acquisition of 3D image data, as well as relative to tracking data acquired by the tracking system and acquisition of cardiac and respiratory cycle information acquired by the EP system.

9. The system of claim 1, further comprising a controller configured to merge the 3D image data with at least one of cardiac or respiratory cycle information to produce a 4D model.

10. The system of claim 1, further comprising a controller operable to calculate a number of image acquisition scans performed by the imaging probe about a longitudinal axis of the imaging probe to produce a 4D model of the imaged anatomy.

11. The system of claim 1, wherein the imaging probe is an intracardiac echocardiography probe.

12. The system of claim 1, wherein the imaging probe includes a transducer array and a motor coupled to the transducer array, the transducer array acquiring the 3D image data, the motor rotating the transducer array so that the 3D image data is acquired at different rotational angles with respect to a longitudinal axis of the imaging probe.

13. The system of claim 1, further comprising a controller configured to gate the acquisition of the 3D image data based on the tracking information.

14. The system of claim 1, wherein the 3D image data is aligned based on the tracking information to produce a 4D model.

15. The system of claim 1, wherein the 3D image data concern a common area of the imaged anatomy and different points in time, and the process combines the 3D image data over time to form a 4D model.

16. The system of claim 1, wherein the tracking system is further configured to track and display a history of each position of the imaging probe during the image acquisition.

17. The system of claim 1, further comprising an imaging system configured to:
receive the 3D image data; and
generate the 3D model using the 3D image data.

18. The system of claim 1, further comprising a steering system and an ablation catheter, the steering system being configured to automatically move the imaging probe along a path of the ablation catheter.

19. The system of claim 1, further comprising a dynamic reference sensor configured to generate motion information of the imaged anatomy, the tracking system being further configured to generate a world coordinate system using the motion information and automatically revise the 3D model, in real-time based on the motion information.

20. The system of claim 19, wherein the motion information comprises at least one of respiratory or cardiac motion.

21. The system of claim 1, wherein the tracking system is configured to receive a second set of 3D image data acquired by a second different imaging system, the tracking system being configured to generate and automatically revise a second 4D model using motion information generated by a dynamic reference sensor.

22. A method of tracking a portion of an imaged anatomy, the method comprising:
acquiring real-time three-dimensional (3D) image data of an imaged anatomy with an imaging probe traveling through an imaged subject;
generating a 3D model of a portion of the imaged anatomy based on the 3D image data;
obtaining real-time tracking information in connection with a position of the imaging probe;
selectively tracking the imaging probe using the tracking information;
receiving electroanatomical information from an EP system; and
mapping the electroanatomical information onto the 3D model based on the tracking information to form a color-coded map of the portion of the imaged anatomy.

23. The method of claim 22, further comprising the step of:
steering movement of the imaging probe and an ablation catheter relative to the tracking information and relative to a four-dimensional (4D) model synchronized in real-time relative to the time reference.

24. The method of claim 22, further comprising:
acquiring at least one of a pre-operative or intra-operative image data using a supplemental imaging system; and
superimposing the pre-operative or intra-operative image data on the 3D model.

25. The method of claim 22, wherein the imaging probe includes a 4D imaging catheter operable to acquire the 3D image data, the method further comprising simultaneously illustrating the 3D image data and the position of the 4D imaging catheter.

26. The method of claim 22, further comprising the step of registering the 3D image data and a tracked position of the imaging probe relative to a dynamic reference sensor located at the imaged anatomy.

27. The method of claim 22, further comprising rotating the imaging probe about a longitudinal axis that extends through a center of the imaging probe.

28. The method of claim 22, further comprising calculating a degree of rotation for a motor to drive movement of the imaging probe about a longitudinal axis of the imaging probe.

29. The method of claim 22, the method further comprising calculating a number of image acquisition scans performed while rotating the imaging probe about a longitudinal axis of the imaging probe to generate the 3D image data of the imaged anatomy.

* * * * *